United States Patent [19]

Lovett

[11] 4,404,064

[45] Sep. 13, 1983

[54] WATER EXTRACTIVE DISTILLATION OF OLEFINICALLY UNSATURATED NITRILES

[75] Inventor: Gordon H. Lovett, Kerrville, Tex.

[73] Assignee: Monsanto Company, St. Louis, Mo.

[21] Appl. No.: 454,752

[22] Filed: Dec. 30, 1982

[51] Int. Cl.³ .................. B01D 3/40; C07C 120/32
[52] U.S. Cl. .................................. 203/84; 203/85;
203/96; 203/98; 203/DIG. 3; 203/DIG. 19;
260/465.3; 260/465.9
[58] Field of Search .................. 203/DIG. 3, 78, 79,
203/42, 84, 85, 83, 96, 97, 98, 99, DIG. 19, 100;
260/465.3, 465.9

[56] References Cited

U.S. PATENT DOCUMENTS

| | | | |
|---|---|---|---|
| 3,328,266 | 6/1967 | Modiano et al. | 203/34 |
| 3,352,764 | 11/1967 | Tyler | 203/85 |
| 3,399,120 | 8/1968 | Lovett | 203/85 |
| 3,445,347 | 5/1969 | Borrel et al. | 203/96 |
| 3,535,849 | 10/1970 | Hausweiler et al. | 203/42 |
| 3,694,322 | 9/1972 | Ikeda et al. | 203/DIG. 3 |
| 4,059,492 | 11/1977 | Hausweiler et al. | 203/DIG. 3 |
| 4,166,008 | 8/1979 | Wu et al. | 203/DIG. 19 |
| 4,238,295 | 12/1980 | Odom | 203/96 |
| 4,334,965 | 6/1982 | Wu | 203/DIG. 19 |
| 4,377,444 | 3/1983 | Wu | 203/DIG. 19 |

Primary Examiner—Wilbur L. Bascomb, Jr.
Attorney, Agent, or Firm—Richard D. Stone; J. C. Logomasini; R. R. Jones

[57] ABSTRACT

The invention provides a process for the recovery and purification of acrylonitrile from acetonitrile and relatively heavy impurities mixture by water extractive distillation and solvent stripping wherein the mixture is fed to approximately the middle of a recovery column, a primary solvent water stream is added to the top of this column and a secondary solvent water stream is added to a point intermediate the mixture feed point and the top of the recovery column; a recovery column bottoms stream comprising water, acetonitrile and acrolein is removed from the bottom of the column and is added to a stripper column; acetonitrile is removed from the upper portion of the stripper column, a primary solvent water stream is removed from the bottom of the stripper column and is sent to the top of the recovery column as the source of the added primary solvent water stream and a secondary solvent water stream is removed from an intermediate point of the solvent stripper and is sent to the recovery column as the source for the added secondary solvent water stream fed to the recovery column and a purified acrylonitrile stream is recovered from the top of the recovery column.

6 Claims, 1 Drawing Figure

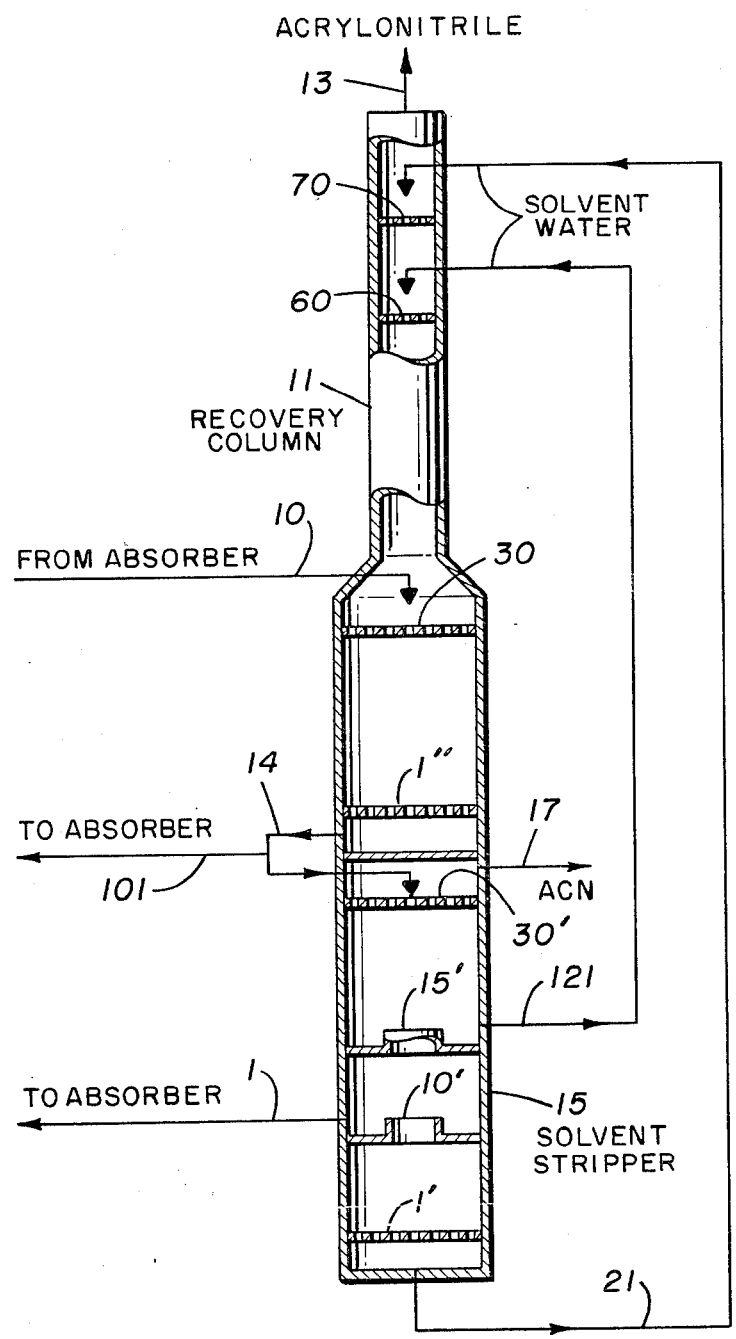

WATER EXTRACTIVE DISTILLATION OF OLEFINICALLY UNSATURATED NITRILES

BACKGROUND OF THE INVENTION

The present invention relates to a process for the purification of olefinically unsaturated nitriles, especially acrylonitrile, by water extractive distillation.

DESCRIPTION OF THE PRIOR ART

A very good and commercially practiced method of producing olefinically unsaturated nitriles is the catalytic reaction of ammonia and an olefin. For example, acrylonitrile and methacrylonitrile may be produced by the vapor phase catalytic oxidation of propylene and isobutylene, respectively, in the presence of ammonia. In these processes, significant amounts of impurities are produced. The production of acrylonitrile from ammonia and propylene results in the formation of significant quantities of acetonitrile, propionitrile, acetone and the like. It is necessary to remove these by-product impurities to produce an unsaturated nitrile suitable for polymerization to other products.

One commonly used method of removing impurities, particularly those that are water miscible from olefinically unsaturated nitrile streams, is extractive distillation of the impure, unsaturated nitrile streams with water as the solvent. Separation of acetonitrile from acrylonitrile is almost impossible by conventional distillation techniques, but is readily accomplished when a lot of liquid water is present. The water alters the relative volatility of acetonitrile to acrylonitrile.

U.S. Pat. No. 3,328,266, the teachings of which are incorporated by reference, taught separation of acrylonitrile from a mixture containing acrylonitrile and acetonitrile. In the presence of large amounts of water the acrylonitrile is recovered as a relatively pure overhead product in an extractive distillation column while the acetonitrile and acrolein are removed from the bottom of this column. The patentee ignored the problem of the separation of acetonitrile from water withdrawn from the bottom of the extractive distillation column. Typically, this stream is sent to a distillation column, the acetonitrile is recovered as a relatively pure stream and a relatively pure water fraction is obtained for recycle to the extractive distillation column.

U.S. Pat. No. 3,445,347, the teachings of which are incorporated by reference, teaches separation of acrylonitrile from acetonitrile by extractive distillation with side stream impurity withdrawal. The side stream, withdrawn from the lower portion of the extractive distillation column, is cooled and sent to a phase separator. A trivial amount of water was recovered by recycle to the top of the extractive distillation column. The amount recycled was 0.032 wt % of the total water added to the top of the column.

The art has long recognized that the large amounts of water required for extractive distillation and the expense of purifying this water for reuse within the extractive distillation zone adds significant costs to processes for purifying unsaturated nitriles by extractive distillation. One attempt to minimize the cost of purifying the acetonitrile contaminated water withdrawn from the bottom of the extractive distillation column was to send a portion of this water to the top of an absorber column. The absorber column is typically used to recover acrylonitrile, along with its by-product acetonitrile, etc., by scrubbing reactor effluent gases with water. The top of an absorber column contains residual waste gas and is usually acrylonitrile free. Sending a portion of the contaminated water from the recovery column bottoms to the top of the absorber column allowed some of the acetonitrile in the contaminated water stream to flash in the absorber and be removed from the process. Such a process is disclosed in U.S. Pat. No. 3,535,849, the teachings of which are incorporated herein by reference. This patent does nothing to alter the mechanics of this extractive distillation process, relatively high purity water is added to the top of the extractive distillation column.

A significant reduction in the cost of operating a water extractive distillation column was disclosed in my U.S. Pat. No. 3,399,120, the teachings of which are incorporated herein by reference. In this patent, the extractive distillation column continues to operate pretty much as before with water added to the top of the column to supply the water needed for water extractive distillation. The economy was realized by supplying much of the heat requirement of the water extractive distillation column with water vapor obtained from the overhead of a stripping zone which purified acetonitrile contaminated water removed from the bottom of the recovery column. The heat savings were achieved by recognizing the energy content of the vapors in the stripper column and allowing these vapors to provide much of the heat requirement for the extractive distillation column.

Somewhat oversimplified, my process minimized the cost of water extractive distillation by making the heat input to the solvent stripper column do double duty. The heat added first provided the heat requirement necessary to operate the solvent stripper and make steam. This steam then reboils the extractive distillation column. All of the water added to the extractive distillation column continued to be relatively pure water added to the very top of the column.

Although the process described in my U.S. Pat. No. 3,399,120 has enjoyed great commercial success and is used throughout the world, it still requires consumption of quite a lot of energy. This is because the nature of water extractive distillation is such that relatively large amounts of water must be present to generate the nonideality of the acrylonitrile-acetonitrile water system. Typically, two to twenty volumes of water are present for every volume of hydrocarbon within a water extractive distillation column used to purify an olefinically unsaturated nitrile.

This water passes through the recovery column from top to bottom and it must be reused. The purification of large amounts of water in the solvent stripper to permit reuse in the water extractive distillation column consumes a lot of energy.

Attempts have been made to improve upon the process of my U.S. Pat. No. 3,399,120. Typical of such improvements is U.S. Pat. No. 4,238,295, the teachings of which are incorporated by reference, which discloses use of the heat contained in the hot water withdrawn from the bottom of the extractive distillation column to heat up other columns or streams in an acrylonitrile plant. Although use of hot streams to warm up cold streams will save some energy, the piping and heat exchangers increase the capital cost of a plant. It is better if the amount of water withdrawn from the bottom of the solvent recovery column and the amount of water added to the very top of this column can be reduced.

Economical operation of the systems described above requires that the steam to the solvent stripper be limited to the minimum needed to completely (99.9+%) strip acetonitrile from the solvent water. While operating in this manner effects a good separation of acetonitrile and acrylonitrile, components less volatile than acetonitrile over water will leak into the acrylonitrile via the solvent water stream. While this leakage could be stopped by using more stream on the stripper, it is the purpose of the present invention to reduce this leakage without increasing the steam consumption above the minimum required for the acrylonitrile-acetonitrile separation.

SUMMARY OF THE INVENTION

Accordingly, the present invention provides a process for the recovery and purification of acrylonitrile from a feed stream comprising acrylonitrile, acetonitrile and relatively heavy impurities consisting of adding said feed stream to a feed point of a recovery column operated at water extractive distillation conditions, the feed point being approximately in the middle of said recovery column; adding to the top of said recovery column a primary solvent water stream from a source hereafter specified and adding a secondary solvent water stream, from a source hereafter specified, to a point intermediate said feed point and top of said recovery column; removing from the bottom of said recovery column a recovery column bottoms stream comprising water, acetonitrile and acrolein; adding said recovery column bottoms stream to a stripper column operated at solvent stripping conditions to remove acetonitrile from the upper portion of said stripper column; removing said primary solvent water stream from the bottom of said stripper column, and sending same to said recovery column, said primary solvent water being reduced in acetonitrile content, but containing at least a portion of said heavy impurities, removing from a point intermediate the top and the bottom of said stripper column a secondary solvent water stream and sending same to said recovery column, said secondary solvent water stream containing relatively less heavy impurity than said primary water stream; and recovering a purified acrylonitrile stream from the top of said recovery column.

BRIEF DESCRIPTION OF THE DRAWING

The drawing is a simplified representation of an extractive distillation column operating in conjunction with a solvent stripper.

For purposes of illustrating the present invention, the drawing will be described with respect to the purification of a crude acrylonitrile stream obtained by the ammoxidation of propylene. The crude acrylonitrile vapors from the reactor were scrubbed with water. The water absorbs the acrylonitrile and water soluble impurities from unreacted hydrocarbons, carbon monoxide, carbon dioxide, and nitrogen, Such crude acrylonitrile stream contains 90 to 95 wt. % water and contains acetonitrile.

Referring to the drawing, the crude process stream comprising acrylonitrile, acetonitrile, acrolein, and other impurities and water is introduced via inlet line 10 into tray 30 of the recovery column 11. Column 11 is shown as having 70 trays. There is no special significance to 70 trays. Depending on tray efficiency, feed composition, and product requirements, more or less trays may be needed. A packed column may also be used.

In conventional operation, water necessary for water extractive distillation is added to the top of recovery column 11 via line 21. Purified acrylonitrile is removed as an overhead vapor fraction from recovery column 11 via line 13, and subjected to conventional workup. This might include cooling, condensing, separating vapor and liquid phases and subsequent purification of recovered acrylonitrile by means not shown. These details are well known in the art and need not be discussed further.

Removed from the bottom of recovery column 11, via line 14, is an aqueous stream substantially free of acrylonitrile but containing significant amounts of acetonitrile, acrolein, and other components with a lower relative volatility than acrylonitrile. This water can be removed and sent directly via line 101 to an absorber column, not shown, in which acrylonitrile is absorbed from cooled, quenched, acrylonitrile reactor effluent vapor.

The water in line 14 not sent to the absorber is sent to the top tray 30 in stripper column 15, shown in the drawing as being directly beneath the recovery column 11. Other configurations are possible as well. Stripper 15 strips acetonitrile and other light organic components from the water to permit its reuse as solvent water in recovery column 11 or for use as lean water in the absorber. Any organics heavier than water remain in the circulating water streams and tend to accumulate in the bottom of stripper column 15. The buildup of heavy organics is controlled by discarding a portion of the water removed from the bottom of stripper 15 by means not shown. A relatively pure water stream may be withdrawn from stripper 15, at tray 10', by line for use in the absorber, not shown.

Relatively volatile organics, primarily acetonitrile, ACN, are removed from the top of stripper 15 via line 17 for further purification or disposal. Preferably, two to four trays are allowed above tray 30' in the stripper to permit some concentration of the acetonitrile stream removed via line 17.

Water may also be removed from stripper column 15 via line 1 for reuse in the absorber. The selection of draw-off point for lean water feed to the absorber, as between lines 1 and 101, will be dictated by local product requirements and the way impurities build up in the recovery column and stripper.

Water is withdrawn from the bottom of stripper 15 via line 21 and sent to tray 70 to provide water for extractive distillation in recovery column 11. In the prior art, practically all of the water requirement is satisfied in this way. In my invention only a portion, called for convenience a primay solvent water stream, is added this way.

From about the mid-point of stripper 15, a solvent water stream with reduced heavy impurity concentration is withdrawn via line 121 from tray 15'. This solvent water, called for convenience a secondary solvent water stream, is sent to tray 60 of the recovery column to satisfy about one-half of the water requirements of this extractive distillation zone recovery column. My invention is use of this secondary solvent water stream.

Preferably, although not shown in the drawing, the recovery column and stripper column are operated as disclosed in my U.S. Pat. No. 3,399,120. Specifically, I prefer to operate with vapors from the solvent stripper column being used to supply, directly, at least some of the heat requirements of the recovery column.

It is also possible to operate with injection of live steam into the base of recovery column 11 by means not shown.

EXAMPLE 1

The acrylonitrile product obtained from the top of the recovery column was subjected to conventional analytical techniques to determine the amount and type of impurities present. These data are reported in Table 1.

TABLE 1

| | | | | | | | COLD QUENCH | | | | | | |
|---|---|---|---|---|---|---|---|---|---|---|---|---|---|
| Run | SW to Top RC | QpH | LWpH | AcN | AcR | FN | 3CNP | AcAM | SN* | PRN | MEAN | CRTN | OXAX |
| 241 | 1 | 4.5 | 6.5 | 0 | 1 | 44 | 16 | 50 | 0 | 0 | 10 | 6 | 7 |
| 242 | 1 | | | 0 | 0 | 64 | 28 | 0 | 513 | 0 | 12 | 17 | 31 |
| 296 | 1 | | | 2 | 0 | 9 | 6 | 1 | 0 | 0 | 20 | 7 | 0 |
| 307 | ½ | | | 5 | 0 | 10 | 5 | 0 | 0 | 0 | 477 | 119 | 0 |
| 244 | 1 | 3.0 | 5.0 | 0 | 20 | 81 | 8 | 0 | 0 | 0 | 10 | 7 | 19 |
| 308 | ½ | | | 0 | 10 | 33 | 5 | 4 | 0 | 0 | 192 | 6 | 0 |
| 291 | 1 | 5.0 | 6.0 | 6 | 1 | 17 | 16 | 3 | 233 | 0 | 18 | 5 | 2 |
| 292 | 1 | | | 0 | 0 | 24 | 10 | 2 | 274 | 0 | 22 | 7 | 6 |
| 306 | 1 | | | 0 | 2 | 22 | 12 | 5 | 0 | 0 | 51 | 33 | 0 |
| 309 | ⅔ | | | 0 | 1 | 14 | 6 | 6 | 0 | 0 | 295 | 1 | 0 | where:
SW = solvent water to top of recovery column
QpH = pH of quench water
LWpH = pH of water going to the absorber
AcN = Acetonitrile
AcR = Acrolein
FN = Fumaronitrile
3CNP = 3-cyanopyridine
AcAM = Acrylamide
SN = Succinonitrile
PRN = Propionitrile
MEAN = Methacrylonitrile
CRTN = Crotonitrile
OXAZ = Oxazole
*Analytical method could not detect the SN; the method was changed after Run 313.

The process of the present invention was tested on a bench scale unit. The bench scale unit available for the test had a recovery column with 70 trays and a solvent stripper with 30 trays. A stream from the absorber was fed to the recovery column at tray 30. Clean water for use in the extractive distillation was taken from the bottom of the solvent stripper and recycled to the top of the recovery column just as solvent water flow in line 21 is shown in the drawing. The secondary solvent water required for extractive distillation was removed from tray 10 of the stripper and added to tray 60 of the recovery column. I would have preferred to operate, as shown in the drawing, i.e., removing water from tray 15' of the stripper and sending it via line 121 to tray 60 of recovery column 11. Unfortunately, there was no sample tap available at tray 15' so I had to use a tap available at tray 10'. There should not be too much difference due to this change.

The feed to the recovery column simulated that feed that would be obtained from a cold quench operation. This means the stream obtained when hot reactor effluent was quenched to about 40° C. and the quenched vapors sent to an absorber. The pH of both the quench liquid and the water used in the absorber change the amount of by-products and impurities that are to be expected so these pH values are reported.

EXAMPLE 2

A number of tests were conducted to see the effect of my invention in a bench scale unit simulating an operation downstream of a hot quench system. A hot quench means that the reactor effluent vapors are quenched to a temperature of 80° to 100° C. This type of operation is more severe, as regards by-product or impurity production.

Results are presented in Table 2.

TABLE 2

| | | | | | | | HOT QUENCH | | | | | | |
|---|---|---|---|---|---|---|---|---|---|---|---|---|---|
| Run | SW to Top RC | QpH | LWpH | AcN | AcR | FN | 3CNP | AcAM | SN* | PRN | MEAN | CRTN | OXAZ |
| 313 | 1 | 3.0 | 6.5 | 22 | 9 | 52 | 39 | 10 | 0 | 0 | 6 | 2 | 141 |
| 314 | ¾ | | | 10 | 1 | 33 | 120 | 1 | 972 | 1 | 8 | 5 | 133 |
| 315 | ¾ | | | 51 | 1 | 93 | 112 | 4 | 1101 | 0 | 10 | 0 | 125 |
| 316 | 1 | 3.0 | 6.5 | 29 | 26 | 104 | 107 | 10 | 1122 | 0 | 3 | 0 | 149 |
| 317A | 1 | | | 40 | 33 | 165 | 130 | 18 | 2516 | 0 | 2 | 1 | 120 |
| 317B | ½ | | | 31 | 13 | 141 | 110 | 18 | 2132 | 0 | 2 | 0 | 115 |

*Analytical method could not detect the SN; the method was changed after Run 313.

My invention was successful in significantly reducing the acrolein concentration for both the hot quench and the cold quench operation. This showed up in the cold quench, comparing Run 244 to Run 308, in which the practice of my invention reduced the AcR concentration by 50%. In the hot quench operation, reductions of about 50%, comparing Runs 316 and 317A to 317B, to over 80%, comparing Runs 313 and 314, were achieved.

I was surprised to learn that the methacrylonitrile, MEAN, and some other impurity concentrations went up significantly when using my invention downstream of a cold quench operation, i.e., Table 1 Data. MEAN concentration did not increase to the same extent in the simulated hot quench operation.

The practice of my invention would be beneficial whenever the presence of significant amounts of acrolein, AcR, could not be tolerated. The increase in MEAN concentration, or of other impurities, is not a drawback if these impurities can be tolerated because they are not detrimental to downstream processing of the acrylonitrile product, or if they are automatically removed from the acrylonitrile by subsequent conventional processing.

The generally accepted limit on acrolein concentration in acrylonitrile product is 10–20 ppm depending on the plant. The reason greater amounts of acrolein cannot be tolerated in the acrylonitrile product is because it affects the color specifications in a negative matter.

The relative amounts of primary water added to the top and secondary added to an upper mid-point below the top of the recovery column can be determined by simple experimentation. Good results can be obtained when 10 to 90% of the water customarily added to the top of the recovery column is added as primary solvent water with 10 to 90% of the water requirement of the recovery column being satisfied by secondary solvent water withdrawn from a mid-point location of the solvent stripper and sent to an upper mid-point of the recovery column. Especially good results can be obtained when $\frac{1}{4}$ to $\frac{3}{4}$ of the water requirement is satisfied in the conventional manner, with primary solvent water, while the remaining water requirements are met with secondary solvent water drawn from about 5 to 20 trays above the bottom of the solvent stripper and added to the recovery column above the feed point and 5 to 20 trays below the top of this column.

The addition and withdrawal points for water streams to the recovery column and from the solvent stripper may vary somewhat. Primary solvent water added to the top of the recovery column is usually added to the top 1–3 trays of this column and preferably to the top tray. This water is typically removed from the bottom or bottom 1 to 5 trays of the solvent stripper. Secondary solvent water added to an upper mid-point of the recovery column is preferably added about half way, plus or minus 50%, between the top of the column and the feed point to the recovery column. It is possible, but usually undesirable, to mix the primary and secondary solvent water streams and add all the water to the top of the recovery column. Such mixing defeats some, but not all, the purposes of my invention. It at least reduces the concentration of heavy impurities in water added to the top of the recovery column. It may contaminate the acrylonitrile product with light impurities. The secondary solvent water has more light ends than the primary solvent, so any light ends present may flash and exit with the acrylonitrile vapor overhead product, if secondary solvent water is mixed with primary solvent water. In my preferred practice, these light ends are absorbed or knocked down in traveling up the recovery column by primary solvent water.

It is also possible to operate the recovery column and stripper column as one large column, as disclosed in my U.S. Pat. No. 3,399,120 in FIG. 2. The same benefits will be achieved in this unified type of operation by providing two sources of solvent water and sending these solvent water streams to two locations near the top of the water extractive distillation column.

I claim:

1. A process for the recovery and purification of acrylonitrile from a feed stream comprising acrylonitrile, acetonitrile, and relatively heavy impurities consisting of
    (a) adding said feed stream to a feed point of a recovery column having a top and a bottom operated at water extractive distillation conditions, the feed point being approximately in the middle of said recovery column;
    (b) adding to the top of said recovery column a primary solvent water stream, from a source hereafter specified, and adding a secondary solvent water stream, from a source hereafter specified, to a point intermediate said feed point and top of said recovery column;
    (c) removing from the bottom of said recovery column a recovery column bottoms stream comprising water, acetonitrile and heavy impurities;
    (d) adding said recovery column bottoms stream to a stripper column having a top and a bottom operated at solvent stripping conditions to remove acetonitrile from an upper portion of said stripper column;
    (e) removing said primary solvent water stream from the bottom of said stripper column, and sending same to said recovery column, said primary solvent water being reduced in acetonitrile content, but containing at least a portion of said heavy impurities;
    (f) removing, from a point intermediate the top and the bottom of said stripper column said secondary solvent water stream and sending same to said recovery column, said secondary solvent water stream containing relatively less heavy impurities than said primary water stream; and
    (g) recovering a purified acrylonitrile stream from the top of said recovery column.

2. Process of claim 1 wherein said primary solvent water stream supplies 10 to 90% of the water required for water extractive distillation within said recovery column and said secondary solvent water stream supplies 90 to 10% of the water requirement of said recovery column.

3. Process of claim 2 wherein said primary solvent water stream supplies 25 to 75% of the water required for water extractive distillation, and said secondary solvent water stream supplies 75 to 25% of said water requirement.

4. Process of claim 1 wherein the recovery column contains approximately 70 actual trays, the feed point to the column is at approximately tray 30, said primary water stream is added to the top at approximately tray 70, and said secondary solvent water stream is added to approximately tray 60.

5. Process of claim 1 wherein the solvent stripper contains approximately 30 trays, the primary solvent water is obtained from the bottom of said solvent stripper, and the secondary solvent water is obtained from about the mid-point stripper.

6. Process of claim 1 wherein the relatively heavy impurity is acrolein.

* * * * *